(12) United States Patent
Andersen

(10) Patent No.: US 9,902,946 B2
(45) Date of Patent: Feb. 27, 2018

(54) ALPHA-AMYLASE VARIANTS AND POLYNUCLEOTIDES ENCODING SAME

(71) Applicant: NOVOZYMES A/S, Bagsvaerd (DK)

(72) Inventor: Carsten Andersen, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/759,068

(22) PCT Filed: Dec. 20, 2013

(86) PCT No.: PCT/EP2013/077678
§ 371 (c)(1),
(2) Date: Jul. 2, 2015

(87) PCT Pub. No.: WO2014/106593
PCT Pub. Date: Jul. 10, 2014

(65) Prior Publication Data
US 2015/0337278 A1    Nov. 26, 2015

Related U.S. Application Data

(60) Provisional application No. 61/752,072, filed on Jan. 14, 2013.

(30) Foreign Application Priority Data

Jan. 3, 2013 (EP) .................................... 13150126

(51) Int. Cl.
| | | |
|---|---|---|
| C12N 9/26 | (2006.01) | |
| C12N 9/28 | (2006.01) | |
| C12Q 1/40 | (2006.01) | |
| D06M 16/00 | (2006.01) | |
| C11D 3/00 | (2006.01) | |
| C07H 21/04 | (2006.01) | |
| C11D 3/386 | (2006.01) | |

(52) U.S. Cl.
CPC ............ *C12N 9/2414* (2013.01); *C11D 3/386* (2013.01); *C12N 9/2417* (2013.01); *C12Y 302/01001* (2013.01)

(58) Field of Classification Search
None
See application file for complete search history.

(56) References Cited

U.S. PATENT DOCUMENTS

| | | | |
|---|---|---|---|
| 6,093,562 A | 7/2000 | Bisgaard-Frantzen | |
| 2007/0190632 A1* | 8/2007 | Bessler | C12N 9/2417 435/183 |
| 2009/0009339 A1 | 1/2009 | Gorrell et al. | |
| 2012/0045822 A1 | 2/2012 | Concar et al. | |
| 2014/0206026 A1* | 7/2014 | Kaasgaard | C12N 9/2414 435/22 |

FOREIGN PATENT DOCUMENTS

| | | |
|---|---|---|
| EP | 1975229 A2 | 1/2008 |
| EP | 2540824 A1 | 1/2013 |
| WO | 96/23873 A1 | 8/1996 |
| WO | 97/41213 A1 | 11/1997 |
| WO | 00/60058 A1 | 10/2000 |
| WO | 01/66712 A2 | 9/2001 |
| WO | 2006/002643 A2 | 1/2006 |
| WO | 2011/080352 A1 | 7/2011 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Declerck et al, 2002, Biologia 57 (11), 203-211.
Nielsen et al, 2000, Biochimi et Biophysi Acta 1543 (2), 253-274.
Leung et al, 1989, Technique 1, 11-15.
Liu et al, 2007, Chemistry Bioengineering 24(3), 58-62.

* cited by examiner

*Primary Examiner* — Iqbal H Chowdhury
(74) *Attorney, Agent, or Firm* — David Fazzolare

(57) ABSTRACT

The present invention relates to alpha-amylase variants. The present invention also relates to polynucleotides encoding the variants; nucleic acid constructs, vectors, and host cells comprising the polynucleotides; and methods of using the variants.

51 Claims, No Drawings

ALPHA-AMYLASE VARIANTS AND POLYNUCLEOTIDES ENCODING SAME

CROSS-REFERENCE TO RELATED APPLICATIONS

This application is a 35 U.S.C. 371 national application of PCT/EP2013/077678 filed Dec. 20, 2013, which claims priority or the benefit under 35 U.S.C. 119 of European application no. 13150126.4 filed Jan. 3, 2013 and U.S. provisional application no. 61/752,072 filed Jan. 14, 2013, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases (alpha-1,4-glucan-4-glucanohydrolases, E.C. 3.2.1.1) constitute a group of enzymes, which catalyses hydrolysis of starch and other linear and branched 1,4-gluosidic oligo- and polysaccharides.

There is a long history of industrial use of alpha-amylases in several known applications such as detergent, baking, brewing, starch liquefaction and saccharification e.g. in preparation of high fructose syrups or as part of ethanol production from starch. These and other applications of alpha-amylases are known and utilize alpha-amylases derived from microorganisms, in particular bacterial alpha-amylases.

WO 2000/060058 discloses the two alpha-amylases AAI-6 and AAI-10 (as SEQ ID NOs 2 and 4 which in the present application are SEQ ID NOs 1 and 2) and discloses thermostable variants thereof.

For environmental reasons it has been increasingly important to lower the temperature in washing, dishwashing and/or cleaning processes. However, most enzymes including the amylases of AAI-6 and AAI-10 have a temperature optimum which is above the temperature usually used in low temperature washing. Alpha-amylase is a key enzyme for use in detergent compositions and its use has become increasingly important for removal of starchy stains during laundry washing or dishwashing. Therefore, it is important to find alpha-amylase variants, which retain their wash performance, stain removal effect and/or activity when the temperature is lowered. Thus, it is desirable to have amylolytic enzymes that can function under low temperature and at the same time preserve or increase other desirable properties such as specific activity (amylolytic activity), stability and/or wash performance.

Thus, it is an object of the present invention to provide alpha-amylases variants which have high performance, in particular high wash performance, at low temperatures and/or which have high stability in detergent compositions and/or which have high amylase activity after storage in detergents.

The present invention provides alpha-amylase variants with improved properties compared to its parent.

SUMMARY OF THE INVENTION

The present invention relates to isolated alpha-amylase variants, comprising an alteration at two or more (several) positions corresponding to W140, W159, W167, Q169, W189, E194, N260, F262, F289, W284, G304, G305, W347, R439, W469, D476 and G477 of the mature polypeptide of SEQ ID NO: 1, wherein each alteration is independently a substitution, deletion or insertion, and wherein the variants have at least 85%, such as at least 90%, or at least 95%, but less than 100% sequence identity with the mature polypeptide of SEQ ID NO: 1 or 2, and wherein the variants have alpha-amylase activity.

The present invention also relates to detergent compositions comprising the variants, isolated polynucleotides encoding the variants; nucleic acid constructs, vectors, and host cells comprising the polynucleotides; and methods of producing the variants.

The present invention also relates to the use of the variants in a cleaning process.

DEFINITIONS

Alpha-amylase: The term "alpha-amylase activity" means the activity of alpha-1,4-glucan-4-glucanohydrolases, E.C. 3.2.1.1, which constitute a group of enzymes, which catalyze hydrolysis of starch and other linear and branched 1,4-glucosidic oligo- and polysaccharides. For purposes of the present invention, alpha-amylase activity is determined according to the procedure described in the Examples. In one aspect, the variants of the present invention have at least 20%, e.g., at least 40%, at least 50%, at least 60%, at least 70%, at least 80%, at least 85%, at least 90%, at least 95%, or at least 100% of the alpha-amylase activity of the mature polypeptide of SEQ ID NO: 1 or 2.

```
SEQ ID NO: 1:
HHDGTNGTIM QYFEWNVPND GQHWNRLHNN AQNLKNAGIT

AIWIPPAWKG TSQNDVGYGA YDLYDLGEFN QKGTVRTKYG

TKAELERAIR SLKANGIQVY GDVVMNHKGG ADFTERVQAV

EVNPQNRNQE VSGTYEIEAW TGFNFPGRGN QHSSFKWRWY

HFDGTDWDQS RQLSNRIYKF RGDGKAWDWE VDTENGNYDY

LMYADVDMNH PEVINELNRW GVWYANTLNL DGFRLDAVKH

IQFSFMRNWL GHVRGQTGKN LFAVAEYWKN DLGALENYLS

KTNWTMSAFD VPLHYNLYQA SNSGGNYDMR NLLNGTLVQR

HPSHAVTFVD NHDTQPGEAL ESFVQGWFKP LAYATILTRE

QGYPQVFYGD YYGIPSDGVP SYRQQIDPLL KARQKYAYGP

QHDYLDHPDV IGWTREGDSS HPKSGLATLI TDGPGGSKRM

YAGLKNAGET WYDITGNRSD TVKIGSDGWG EFHVNDGSVS

IYVQK

SEQ ID NO: 2:
HHDGTNGTIM QYFEWNVPND GQHWNRLHNN AQNLKNAGIT

AIWIPPAWKG TSQNDVGYGA YDLYDLGEFN QKGTVRTKYG

TKAELERAIR SLKANGIQVY GDVVMNHKGG ADFTERVQAV

EVNPQNRNQE VSGTYQIEAW TGFNFPGRGN QHSSFKWRWY
```

```
                            -continued
HFDGTDWDQS  RQLANRIYKF  RGDGKAWDWE  VDTENGNYDY

LMYADVDMDH  PEVINELNRW  GVWYANTLNL  DGFRLDAVKH

IKFSFMRDWL  GHVRGQTGKN  LFAVAEYWKN  DLGALENYLS

KTNWTMSAFD  VPLHYNLYQA  SNSSGNYDMR  NLLNGTLVQR

HPSHAVTFVD  NHDTQPGEAL  ESFVQGWFKP  LAYATILTRE

QGYPQVFYGD  YYGIPSDGVP  SYRQQIDPLL  KARQQYAYGR

QHDYFDHWDV  IGWTREGNAS  HPNSGLATIM  SDGPGGSKWM

YVGRQKAGEV  WHDMTGNRSG  TVTINQDGWG  HFFVNGGSVS

VWVKR
```

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has alpha-amylase activity. In one aspect, a fragment contains at least 470 amino acid residues, at least 475 amino acid residues, or at least 480 amino acid residues.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant of the present invention that is improved compared to the parent which parent only differs from the variant in the one or more claimed positions. Alternatively, it is compared to the mature polypeptide of SEQ ID NO: 1 or 2. Such improved properties include, but are not limited to, catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, and thermo stability, and improved wash performance, particularly improved wash performance at low temperatures, such as temperatures between 5° C. and 35° C., such as below 35° C., or below 30° C., or even below 20° C., or at temperatures below 15° C., or even at temperatures below 10° C. Another property that may be improved in the variants is the stability during storage in detergent compositions.

Wash performance: In the present context the term "wash performance" is used as an enzyme's ability to remove starch or starch-containing stains present on the object to be cleaned during e.g. laundry or hard surface cleaning, such as dish wash. The wash performance may be quantified by calculating the so-called delta remission value (ΔRem) as described in the definition herein.

Improved wash performance: The term "improved wash performance" is defined herein as a variant enzyme displaying an alteration of the wash performance of an amylase variant relative to the wash performance of the parent amylase or relative to the alpha-amylase having the amino acid sequence shown in SEQ ID NO 1 or 2, e.g. by increased stain removal. The term "wash performance" includes cleaning in general e.g. hard surface cleaning as in dish wash, but also wash performance on textiles such as laundry, and also industrial and institutional cleaning. Improved wash performance may be measured by comparing of the so-called delta remission value (ΔRem) as described in the definition herein.

Low temperature: "Low temperature" is a temperature of 5-35° C., preferably 5-30° C., more preferably 5-25° C., more preferably 5-20° C., most preferably 5-15° C., and in particular 5-10° C. In a preferred embodiment, "Low temperature" is a temperature of 10-35° C., preferably 10-30° C., more preferably 10-25° C., most preferably 10-20° C., and in particular 10-15° C.

Delta remission value (ΔRem): The terms "Delta remission" or "Delta remission value" are defined herein as the result of a reflectance or remission measurement at 460 nm of a test material, e.g. a swatch CS-28 (Center For Testmaterials BV, P.O. Box 120, 3133 KT Vlaardingen, the Netherlands) or a hard surface. The swatch is measured with at least one other swatch, washed under identical conditions, as background. The delta remission is the remission value of the test material washed with amylase subtracted the remission value of the test material washed without amylase.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 485 of SEQ ID NO: 1 or 2.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having alpha-amylase activity.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" means an alpha-amylase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1 or 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type alpha-amylase: The term "wild-type" alpha-amylase means an alpha-amylase expressed by a naturally occurring microorganism, such as a bacterium, archaea, yeast, or filamentous fungus found in nature.

Conventions for Designation of Variants

For purposes of the present invention, the mature polypeptide disclosed in SEQ ID NO: 1 is used to determine the corresponding amino acid residue in another alpha-amylase. The amino acid sequence of another alpha-amylase is aligned with the mature polypeptide disclosed in SEQ ID NO: 1, and based on the alignment, the amino acid position number corresponding to any amino acid residue in the mature polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". In situations where the amino acid at a given position may be substituted for any other amino acid it is designated T226ACDEFGHIKLMNPQRSWVY. Accordingly, this means that threonine at position 226 may be substituted with one amino acid selected from the group of A, C, D, E, F, G, H, I, K, L, M, N, P, Q, R, S, W, V or Y. Likewise, in situations where the amino acid at a given position may be substituted for one amino acid selected from a specific group of amino acids, e.g. where the threonine at position 226 may be substituted with any of tyrosine, phenylalanine or histidine it is designated T226YFH. The different alterations at a given position may also be separated by a comma, e.g., "Arg170Tyr,Glu" or "R170Y,E" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple Alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

DETAILED DESCRIPTION OF THE INVENTION

Variants

The present invention relates to isolated alpha-amylase variants, comprising an alteration at one, two or more (several) positions corresponding to positions W140; W159; W167, Q169, W189, E194, N260, F262, F289, W284, G304, G305, W347, R439, W469, D476 and G477 of the mature polypeptide of SEQ ID NO: 1, wherein each alteration is independently a substitution, deletion or insertion, and wherein the variant has at least 85%, such as at least 90%, or at least 95%, but less than 100% sequence identity with the mature polypeptide of SEQ ID NO: 1 and wherein the variant has alpha-amylase activity.

The present invention also relates to isolated alpha-amylase variants, comprising an alteration at one, two or more (several) positions corresponding to positions W140; W159; W167, Q169, W189, E194, N260, F262, F289, W284, S304, G305, W347, W439, W469, G476 and G477 of the mature polypeptide of SEQ ID NO: 2, wherein each alteration is independently a substitution, deletion or insertion, and wherein the variant has at least 85%, such as at least 90%, or at least 95%, but less than 100% sequence identity with the mature polypeptide of SEQ ID NO: 2 and wherein the variant has alpha-amylase activity.

Hereby, variants are provided which have improved washing performance at low temperature compared to the parent alpha-amylase or compared to the alpha-amylase of SEQ ID NO: 1 or 2.

In an embodiment, the alterations are substitutions.

In another embodiment of the invention the variants may comprise alterations at three or more of said positions mentioned above.

In yet another embodiment of the invention the variants may comprise alterations at four or more of said positions mentioned above.

In yet another embodiment of the invention the variants may comprise alterations at five or more of said positions mentioned above.

In yet another embodiment of the invention the variants may comprise alterations at six or more of said positions mentioned above.

In yet another embodiment of the invention the variants may comprise alterations at seven or more of said positions mentioned above.

In yet another embodiment of the invention the variants may comprise alterations at eight or more of said positions mentioned above.

In yet another embodiment of the invention the variants may comprise alterations at nine or more of said positions mentioned above.

In yet another embodiment of the invention the variants may comprise alterations at ten or more of said positions mentioned above.

In one aspect of the invention, one of the above mentioned one, two or more substitutions may be a substitution at position 140 when using SEQ ID NO: 1 for numbering. The substitution may be any of W140ACDEFGHIKLMNPQRSTVY, but preferably it is W140YFH and most preferred it is W140Y.

In another aspect of the invention, one of the above mentioned one, two or more substitutions may be a substitution at position 159 when using SEQ ID NO: 1 for numbering. The substitution may be any of WI59ACDEFGHIKLMNPQRSTVY preferably W159YFH.

In one embodiment of the invention, one of the above mentioned one, two or more substitutions may be a substitution at position 167 when using SEQ ID NO: 1 for numbering. The substitution may be any of W167ACDEFGHIKLMNPQRSTVY, preferably W167YHF.

In one embodiment of the invention, one of the above mentioned one, two or more substitutions may be a substitution at position 169 when using SEQ ID NO: 1 for numbering. The substitution may be any of Q169ACDEFGHIKLMNPWRSTVY.

In one embodiment of the invention, one of the above mentioned one, two or more substitutions may be a substitution at position 189 when using SEQ ID NO: 1 for numbering. The substitution may be any of W189ACDEFGHIKLMNPQRSTVY. Alternatively E190P may be substituted.

In one embodiment of the invention, one of the above mentioned one, two or more substitutions may be a substitution at position 194 when using SEQ ID NO: 1 for numbering. The substitution may be any of E194ACDWFGHIKLMNPQRSTVY, preferably E194D.

In one embodiment of the invention, one of the above mentioned one, two or more substitutions may be a substitution at position 260 when using SEQ ID NO: 1 for numbering. The substitution may be any of N260ACFGHIKLMWPQ RSTVY, preferably N260G or N260P or N260A.

In one embodiment of the invention, one of the above mentioned one, two or more substitutions may be a substitution at position 262 when using SEQ ID NO: 1 for numbering. The substitution may be any of F262ACDEWGHIKLMNPQRSTVY, preferably F262P or F262G.

In one embodiment of the invention, one of the above mentioned one, two or more substitutions may be a substitution at position 284 when using SEQ ID NO: 1 for numbering. The substitution may be any of W284ACDEFGHIKLMNPQRSTVY, preferably W284G or W284H.

In one embodiment of the invention, one of the above mentioned one, two or more substitutions may be a substitution at position F289 when using SEQ ID NO: 1 for numbering. The substitution may be any of F289ACDEWGHIKLMNPQRSTVY, preferably F289H.

In one embodiment of the invention, one of the above mentioned one, two or more substitutions may be a substitution at position 304 when using SEQ ID NO: 1 for numbering. The substitution may be any of G304ACEFHIKLMPQRWTVY, preferably it is G304K or G304R or G304Q or G304E, and most preferred it is G304K. In other amylases, e.g. the amylase of SEQ ID NO: 2, the natural occurring amino acid in this position is S. So, when using such other amylases as a starting point for the variants, the substitution may be any of S304ACEFHIKLMPQRWTVY; preferably it is S304K or S304R or S304Q or S304E, and most preferred it is S304K.

In another embodiment of the invention, one of the above mentioned one, two or more substitutions may be a substitution at position 305 when using SEQ ID NO: 1 for numbering. The substitution may be any of G305ACEFWHIKLMPQRTVY, preferably it is G305K or G305R or G305Q or G305E, and most preferred it is G305K.

In one embodiment of the invention, one of the above mentioned one, two or more substitutions may be a substitution at position 347 when using SEQ ID NO: 1 for numbering. The substitution may be any of W347ACDEFGHIKLMNPQRSTVY, preferably W347Y or W347F or W347H.

In another embodiment of the invention, one of the above mentioned one, two or more substitutions may be a substitution at position 439 when using SEQ ID NO: 1 for numbering. The substitution may be any of R439ACDEFGHIKLMNPQSTVY; preferably it is a substitution of R439N or R439Q. In other amylases, e.g. the amylase of SEQ ID NO: 2, the natural occurring amino acid in this position is W. So, when using such other amylases as a starting point for the variants, the substitution may be any of W439ACDEFGHIKLMNPQRSTVY, preferably it is a substitution of W439N or W439Q.

In another embodiment of the invention, one of the above mentioned one, two or more substitutions may be a substitution at position 469 when using SEQ ID NO: 1 for numbering. The substitution may be any W469ACDEFGHIKLMNPQRSTVY; preferably it is W469T or W469N.

In another embodiment of the invention, one of the above mentioned one, two or more substitutions may be a substitution at position 476 when using SEQ ID NO: 1 for numbering. The substitution may be any of D476ACEFHIKLMPQRTVWY, preferably it is D476K or D476R or D476Q or D476E, and most preferred it is D476K. In other amylases, e.g. the amylase of SEQ ID NO: 2, the natural occurring amino acid in this position is G. So the substitution may be any of G476ACEFHIKLMPQRTVWY, preferably it is G476K or G476R or G476Q or G476E, and most preferred it is G476K.

In another embodiment of the invention, one of the above mentioned one, two or more substitutions may be a substitution at position 477 when using SEQ ID NO: 1 for numbering. The substitution may be any of G477ACEFHIKLMPQRTVWY, preferably it is G477K or G477R or G477Q or G477E, and most preferred it is G477K.

The inventor of the present invention contemplates that variants having at least 85% sequence identity to SEQ ID NO: 1 or 2 and having one, two or more of the above mentioned substitutions have particularly high performance at low temperature washing. In particular, for variants of SEQ ID NO: 1 or 2 or variants having at least 85% sequence identity to SEQ ID NO: 1 or 2 it is an advantage to substitute tryptophans on the surface of the molecule, e.g. the tryptophans at positions 140, 159, 167, 189, 284, 347, 439, 469 e.g. with any amino acids, such as tyrosine, phenylalanine or histidine, and to substitute glycines or serines in the vicinity (on the surface) of these tryptophans with a larger amino acid, such as glutamic acid, glutamine, arginine or lysine. This is e.g. the substitutions of G304EQRK or G305EQRK or D476EQRK or G477EQRK. Such substitutions decrease the substrate binding of the alpha-amylase and improve the wash performance at low temperature washing.

The variants of the invention may further comprise a deletion of two positions selected from the group consisting of R181, G182, D183 and G184 when using SEQ ID NO: 1 for numbering, preferably a deletion of R181+G182, or of G182+D183 or of R181+G184 or of G182+G184, or more preferred of D183+G184. It has been found that such a double deletion stabilizes the molecule.

The variants of the invention may further comprise at least one of the substitutions selected from the group consisting of G109A, G149A, K179L, G186A, E190P, N195F, M202LIT, V206YF, Y243F, S244QAEDN and N209D and when using SEQ ID NO: 1 for numbering. These substitutions likewise provide improved stability to the alpha-amylases.

In another aspect, the invention relates to variants which comprise modifications in the positions, corresponding to the positions of the polypeptide of SEQ ID NO: 1, selected from the group consisting of:

W140Y+Y160S
W140Y+E194D
W140Y+N260P
W140Y+G304K
W140Y+G304R
W140Y+R439T
W140Y+W469T
W140Y+D476K
W140Y+G477R
Y160S+E194D
Y160S+E212D
Y160S+N260P
Y160S+G304K
Y160S+G304R
Y160S+R439T
Y160S+W469T
Y160S+D476K
Y160S+G477R
N260P+G304K
N260P+G305R
N260P+R439K
N260P+W469R
N260P+D476K
N260P+G477R
W284G+G304K
W284G+G305R
W284G+R439N
W284G+W469T
W284G+D476K
W284G+G477R
L279T+W284G+H324N+G304K
L279T+W284G+H324N+G305R
L279T+W284G+H324N+R439N
L279T+W284G+H324N+W469T
L279T+W284G+H324N+D476K
L279T+W284G+H324N+G477R
G304K+R439K
G304K+W469R
G304K+D476K
G304K+G477R
G305K+R439K
G305K+W469R
G305K+D476K
G305K+G477R
R439N+W469R
R439N+D476K
R439N+G477R
W469T+D476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+D476K
W140Y+E212D+G305K+D476K
W140Y+G305K+R439N+D476K
W140Y+G305K+W469T+D476K
W140Y+G304R+D476K
W140Y+N260P+G304R+G477K
W140Y+E212D+G304R+G477K
W140Y+G304R+R439N+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+R439N+G477K and
W140Y+G305K+W469T+G477K wherein the variants have at least 85% and less than 100% sequence identity to the alpha-amylase of SEQ ID NO: 1. These variants preferably further comprise a deletion of the amino acids occupying positions R181+G182, or of G182+D183, or most preferred of D183+G184.

In another aspect, the invention relates to variants which comprise modifications in the positions, corresponding to the positions of the polypeptide of SEQ ID NO: 1, selected from the group consisting of:

W140Y+Y160S
W140Y+E194D
W140Y+N260P
W140Y+G304K
W140Y+G304R
W140Y+R439T
W140Y+W469T
W140Y+D476K
W140Y+G477R
Y160S+E194D
Y160S+E212D
Y160S+N260P
Y160S+G304K
Y160S+G304R
Y160S+R439T
Y160S+W469T
Y160S+D476K
Y160S+G477R
N260P+G304K
N260P+G305R
N260P+R439K
N260P+W469R
N260P+D476K
N260P+G477R

W284G+G304K
W284G+G305R
W284G+R439N
W284G+W469T
W284G+D476K
W284G+G477R
L279T+W284G+H324N+G304K
L279T+W284G+H324N+G305R
L279T+W284G+H324N+R439N
L279T+W284G+H324N+W469T
L279T+W284G+H324N+D476K
L279T+W284G+H324N+G477R
G304K+R439K
G304K+W469R
G304K+D476K
G304K+G477R
G305K+R439K
G305K+W469R
G305K+G477R
R439N+W469R
R439N+D476K
R439N+G477R
W469T+D476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+D476K
W140Y+E212D+G305K+D476K
W140Y+G305K+R439N+D476K
W140Y+G305K+W469T+D476K
W140Y+G304R+D476K
W140Y+N260P+G304R+G477K
W140Y+E212D+G304R+G477K
W140Y+G304R+R439N+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+R439N+G477K and
W140Y+G305K+W469T+G477K
wherein the variants have at least 90% and less than 100% sequence identity to the alpha-amylase of SEQ ID NO: 1.

In another aspect, the invention relates to variants which comprise modifications in the positions, corresponding to the positions of the polypeptide of SEQ ID NO: 1, selected from the group consisting of:
W140Y+Y160S
W140Y+E194D
W140Y+N260P
W140Y+G304K
W140Y+G304R
W140Y+R439T
W140Y+W469T
W140Y+D476K
W140Y+G477R
Y160S+E194D
Y160S+E212D
Y160S+N260P
Y160S+G304K
Y160S+G304R
Y160S+R439T
Y160S+W469T
Y160S+D476K
Y160S+G477R
N260P+G304K
N260P+G305R
N260P+R439K
N260P+W469R
N260P+D476K
N260P+G477R
W284G+G304K
W284G+G305R
W284G+R439N
W284G+W469T
W284G+D476K
W284G+G477R
L279T+W284G+H324N+G304K
L279T+W284G+H324N+G305R
L279T+W284G+H324N+R439N
L279T+W284G+H324N+W469T
L279T+W284G+H324N+D476K
L279T+W284G+H324N+G477R
G304K+R439K
G304K+W469R
G304K+D476K
G304K+G477R
G305K+R439K
G305K+W469R
G305K+D476K
G305K+G477R
R439N+W469R
R439N+D476K
R439N+G477R
W469T+D476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+D476K
W140Y+E212D+G305K+D476K
W140Y+G305K+R439N+D476K
W140Y+G305K+W469T+D476K
W140Y+G304R+D476K
W140Y+N260P+G304R+G477K
W140Y+E212D+G304R+G477K
W140Y+G304R+R439N+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+R439N+G477K and
W140Y+G305K+W469T+G477K
wherein the variants has at least 95% and less than 100% sequence identity to the alpha-amylase of SEQ ID NO: 1.

In another aspect, the invention relates to variants which comprise modifications in the positions, corresponding to the positions of the polypeptide of SEQ ID NO: 1, selected from the group consisting of:
W140Y+Y160S
W140Y+E194D
W140Y+N260P
W140Y+G304K
W140Y+G304R
W140Y+W469T
W140Y+D476K W140Y+G477R
Y160S+E194D
Y160S+E212D
Y160S+N260P
Y160S+G304K
Y160S+G304R
Y160S+R439T
Y160S+W469T
Y160S+D476K
Y160S+G477R
N260P+G304K
N260P+G305R
N260P+R439K
N260P+W469R
N260P+D476K
N260P+G477R
W284G+G304K
W284G+G305R
W284G+R439N
W284G+W469T
W284G+D476K
W284G+G477R
L279T+W284G+H324N+G304K
L279T+W284G+H324N+G305R
L279T+W284G+H324N+R439N
L279T+W284G+H324N+W469T
L279T+W284G+H324N+D476K
L279T+W284G+H324N+G477R
G304K+R439K
G304K+W469R
G304K+D476K
G304K+G477R
G305K+R439K
G305K+W469R
G305K+D476K
G305K+G477R
R439N+W469R
R439N+D476K
R439N+G477R
W469T+D476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+D476K
W140Y+E212D+G305K+D476K
W140Y+G305K+R439N+D476K
W140Y+G305K+W469T+D476K
W140Y+G304R+D476K
W140Y+N260P+G304R+G477K
W140Y+E212D+G304R+G477K
W140Y+G304R+R439N+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+R439N+G477K and
W140Y+G305K+W469T+G477K
wherein the variants has at least 97% and less than 100% sequence identity to the alpha-amylase of SEQ ID NO: 1.

In another aspect, the invention relates to variants which comprise modifications in the positions, corresponding to the positions of the polypeptide of SEQ ID NO: 1, selected from the group consisting of:
W140Y+Y160S
W140Y+E194D
W140Y+N260P
W140Y+G304K
W140Y+G304R
W140Y+R439T
W140Y+W469T
W140Y+D476K
W140Y+G477R
Y160S+E194D
Y160S+E212D
Y160S+N260P
Y160S+G304K
Y160S+G304R
Y160S+R439T
Y160S+W469T
Y160S+D476K
Y160S+G477R
N260P+G304K
N260P+G305R
N260P+R439K
N260P+W469R
N260P+D476K
N260P+G477R
W284G+G304K
W284G+G305R
W284G+R439N
W284G+W469T
W284G+D476K
W284G+G477R
L279T+W284G+H324N+G304K
L279T+W284G+H324N+G305R
L279T+W284G+H324N+R439N
L279T+W284G+H324N+W469T
L279T+W284G+H324N+D476K
L279T+W284G+H324N+G477R
G304K+R439K
G304K+W469R
G304K+D476K
G304K+G477R
G305K+R439K
G305K+W469R
G305K+D476K
G305K+G477R
R439N+W469R
R439N+D476K
R439N+G477R
W469T+D476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+D476K
W140Y+E212D+G305K+D476K
W140Y+G305K+R439N+D476K
W140Y+G305K+W469T+D476K
W140Y+G304R+D476K
W140Y+N260P+G304R+G477K
W140Y+E212D+G304R+G477K
W140Y+G304R+R439N+G477K W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+R439N+G477K and
W140Y+G305K+W469T+G477K wherein the variants has at least 98% and less than 100% sequence identity to the alpha-amylase of SEQ ID NO: 1.

In yet another aspect, the invention relates to variants wherein the alterations consist of the following alterations in SEQ ID NO: 1:

W140Y+Y160S
W140Y+E194D
W140Y+N260P
W140Y+G304K
W140Y+G304R
W140Y+R439T
W140Y+W469T
W140Y+D476K
W140Y+G477R
Y160S+E194D
Y160S+E212D
Y160S+N260P
Y160S+G304K
Y160S+G304R
Y160S+R439T
Y160S+W469T
Y160S+D476K
Y160S+G477R
N260P+G304K
N260P+G305R
N260P+R439K
N260P+W469R
N260P+D476K
N260P+G477R
W284G+G304K
W284G+G305R
W284G+R439N
W284G+W469T
W284G+D476K
W284G+G477R
L279T+W284G+H324N+G304K
L279T+W284G+H324N+G305R
L279T+W284G+H324N+R439N
L279T+W284G+H324N+W469T
L279T+W284G+H324N+D476K
L279T+W284G+H324N+G477R
G304K+R439K
G304K+W469R
G304K+D476K
G304K+G477R
G305K+R439K
G305K+W469R
G305K+D476K
G305K+G477R
R439N+W469R
R439N+D476K
R439N+G477R
W469T+D476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K

W140Y+N260P+G305K+D476K
W140Y+E212D+G305K+D476K
W140Y+G305K+R439N+D476K
W140Y+G305K+W469T+D476K
W140Y+G304R+D476K
W140Y+N260P+G304R+G477K
W140Y+E212D+G304R+G477K
W140Y+G304R+R439N+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+R439N+G477K and
W140Y+G305K+W469T+G477K In yet another aspect, the invention relates to variants wherein the alterations consist of the alterations in SEQ ID NO: 2:

W140Y+Y160S
W140Y+E194D
W140Y+N260P
W140Y+G304K
W140Y+G304R
W140Y+W439T
W140Y+W469T
W140Y+G476K
W140Y+G477R
Y160S+E194D
Y160S+E212D
Y160S+N260P
Y160S+G304K
Y160S+G304R
Y160S+W439T
Y160S+W469T
Y160S+G476K
Y160S+G477R
N260P+G304K
N260P+G305R
N260P+W439K
N260P+W469R
N260P+G476K
N260P+G477R
W284G+G304K
W284G+G305R
W284G+W439R
W284G+W469T
W284G+G476K
W284G+G477R
L279T+W284G+H324N+G304K
L279T+W284G+H324N+G305R
L279T+W284G+H324N+W439R
L279T+W284G+H324N+W469T
L279T+W284G+H324N+G476K
L279T+W284G+H324N+G477R
G304K+W439K
G304K+W469R
G304K+G476K
G304K+G477R
G305K+W439K
G305K+W469R
G305K+G476K
G305K+G477R
W439R+W469R
W439R+G476K
W439R+G477R
W469T+G476K
W469T+G477R

W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+G476K
W140Y+E212D+G305K+G476K
W140Y+G305K+W439R+G476K
W140Y+G305K+W469T+G476K
W140Y+G304R+G476K
W140Y+N260P+G304R+G477K
W140Y+E212D+G304R+G477K
W140Y+G304R+W439R+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+W439R+G477K and
W140Y+G305K+W469T+G477K In yet another aspect, the invention relates to variants which comprise modifications in the positions, corresponding to the positions of the polypeptide of SEQ ID NO: 2, selected from the group consisting of:

W140Y+Y160S
W140Y+E194D
W140Y+N260P
W140Y+G304K
W140Y+G304R
W140Y+W439T
W140Y+W469T
W140Y+G476K
W140Y+G477R
Y160S+E194D
Y160S+E212D
Y160S+N260P
Y160S+G304K
Y160S+G304R
Y160S+W439T
Y160S+W469T
Y160S+G476K
Y160S+G477R
N260P+G304K
N260P+G305R
N260P+W439K
N260P+W469R
N260P+G476K
N260P+G477R
W284G+G304K
W284G+G305R
W284G+W439R
W284G+W469T
W284G+G476K
W284G+G477R
L279T+W284G+H324N+G304K
L279T+W284G+H324N+G305R
L279T+W284G+H324N+W439R
L279T+W284G+H324N+W469T
L279T+W284G+H324N+G476K
L279T+W284G+H324N+G477R
G304K+W439K
G304K+W469R
G304K+G476K
G304K+G477R
G305K+W439K
G305K+W469R
G305K+G476K
G305K+G477R
W439R+W469R
W439R+G476K
W439R+G477R
W469T+G476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+G476K
W140Y+E212D+G305K+G476K
W140Y+G305K+W439R+G476K
W140Y+G305K+W469T+G476K
W140Y+G304R+G476K
W140Y+N260P+G304R+G477K
W140Y+E212D+G304R+G477K
W140Y+G304R+W439R+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+W439R+G477K and
W140Y+G305K+W469T+G477K wherein the variants has at least 85% and less than 100% sequence identity to the alpha-amylase of SEQ ID NO: 2.

In another aspect, the invention relates to variants which comprise modifications in the positions, corresponding to the positions of the polypeptide of SEQ ID NO: 2, selected from the group consisting of:

W140Y+Y160S
W140Y+E194D
W140Y+N260P
W140Y+G304K
W140Y+G304R
W140Y+W439T
W140Y+W469T
W140Y+G476K
W140Y+G477R
Y160S+E194D
Y160S+E212D
Y160S+N260P
Y160S+G304K
Y160S+G304R
Y160S+W439T
Y160S+W469T
Y160S+G476K
Y160S+G477R
N260P+G304K
N260P+G305R
N260P+W439K
N260P+W469R
N260P+G476K
N260P+G477R
W284G+G304K
W284G+G305R
W284G+W439R
W284G+W469T
W284G+G476K
W284G+G477R
L279T+W284G+H324N+G304K
L279T+W284G+H324N+G305R
L279T+W284G+H324N+W439R

L279T+W284G+H324N+W469T
L279T+W284G+H324N+G476K
L279T+W284G+H324N+G477R
G304K+W439K
G304K+W469R
G304K+G476K
G304K+G477R
G305K+W439K
G305K+W469R
G305K+G476K
G305K+G477R
W439R+W469R
W439R+G476K
W439R+G477R
W469T+G476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+G476K
W140Y+E212D+G305K+G476K
W140Y+G305K+W439R+G476K
W140Y+G305K+W469T+G476K
W140Y+G304R+G476K
W140Y+N260P+G304R+G477K
W140Y+E212D+G304R+G477K
W140Y+G304R+W439R+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+W439R+G477K and
W140Y+G305K+W469T+G477K wherein the variants has at least 90% and less than 100% sequence identity to the alpha-amylase of SEQ ID NO: 2.

In another aspect, the invention relates to variants which comprise modifications in the positions, corresponding to the positions of the polypeptide of SEQ ID NO: 2, selected from the group consisting of:

W140Y+Y160S
W140Y+E194D
W140Y+N260P
W140Y+G304K
W140Y+G304R
W140Y+W439T
W140Y+W469T
W140Y+G476K
W140Y+G477R
Y160S+E194D
Y160S+E212D
Y160S+N260P
Y160S+G304K
Y160S+G304R
Y160S+W439T
Y160S+W469T
Y160S+G476K
Y160S+G477R
N260P+G304K
N260P+G305R
N260P+W439K
N260P+W469R
N260P+G476K
N260P+G477R
W284G+G304K
W284G+G305R
W284G+W439R
W284G+W469T
W284G+G476K
W284G+G477R
L279T+W284G+H324N+G304K
L279T+W284G+H324N+G305R
L279T+W284G+H324N+W439R
L279T+W284G+H324N+W469T
L279T+W284G+H324N+G476K
L279T+W284G+H324N+G477R
G304K+W439K
G304K+W469R
G304K+G476K
G304K+G477R
G305K+W439K
G305K+W469R
G305K+G476K
G305K+G477R
W439R+W469R
W439R+G476K
W439R+G477R
W469T+G476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+G476K
W140Y+E212D+G305K+G476K
W140Y+G305K+W439R+G476K
W140Y+G305K+W469T+G476K
W140Y+G304R+G476K
W140Y+N260P+G304R+G477K
W140Y+E212D+G304R+G477K
W140Y+G304R+W439R+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+W439R+G477K and
W140Y+G305K+W469T+G477K wherein the variants has at least 95% and less than 100% sequence identity to the alpha-amylase of SEQ ID NO: 2.

In another aspect, the invention relates to variants which comprise modifications in the positions, corresponding to the positions of the polypeptide of SEQ ID NO: 2, selected from the group consisting of:

W140Y+Y160S
W140Y+E194D
W140Y+N260P
W140Y+G304K
W140Y+G304R
W140Y+W439T
W140Y+W469T
W140Y+G476K
W140Y+G477R
Y160S+E194D
Y160S+E212D
Y160S+N260P
Y160S+G304K
Y160S+G304R
Y160S+W439T

Y160S+W469T
Y160S+G476K
Y160S+G477R
N260P+G304K
N260P+G305R
N260P+W439K
N260P+W469R
N260P+G476K
N260P+G477R
W284G+G304K
W284G+G305R
W284G+W439R
W284G+W469T
W284G+G476K
W284G+G477R
L279T+W284G+H324N+G304K
L279T+W284G+H324N+G305R
L279T+W284G+H324N+W439R
L279T+W284G+H324N+W469T
L279T+W284G+H324N+G476K
L279T+W284G+H324N+G477R
G304K+W439K
G304K+W469R
G304K+G476K
G304K+G477R
G305K+W439K
G305K+W469R
G305K+G476K
G305K+G477R
W439R+W469R
W439R+G476K
W439R+G477R
W469T+G476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+G476K
W140Y+E212D+G305K+G476K
W140Y+G305K+W439R+G476K
W140Y+G305K+W469T+G476K
W140Y+G304R+G476K
W140Y+N260P+G304R+G477K
W140Y+E212D+G304R+G477K
W140Y+G304R+W439R+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+W439R+G477K and
W140Y+G305K+W469T+G477K
wherein the variants has at least 96% and less than 100% sequence identity to the alpha-amylase of SEQ ID NO: 2.

In another aspect, the invention relates to variants which comprise modifications in the positions, corresponding to the positions of the polypeptide of SEQ ID NO: 2, selected from the group consisting of:
W140Y+Y160S
W140Y+E194D
W140Y+N260P
W140Y+G304K
W140Y+G304R
W140Y+W439T
W140Y+W469T
W140Y+G476K
W140Y+G477R
Y160S+E194D
Y160S+E212D
Y160S+N260P
Y160S+G304K
Y160S+G304R
Y160S+W439T
Y160S+W469T
Y160S+G476K
Y160S+G477R
N260P+G304K
N260P+G305R
N260P+W439K
N260P+W469R
N260P+G476K
N260P+G477R
W284G+G304K
W284G+G305R
W284G+W439R
W284G+W469T
W284G+G476K
W284G+G477R
L279T+W284G+H324N+G304K
L279T+W284G+H324N+G305R
L279T+W284G+H324N+W439R
L279T+W284G+H324N+W469T
L279T+W284G+H324N+G476K
L279T+W284G+H324N+G477R
G304K+W439K
G304K+W469R
G304K+G476K
G304K+G477R
G305K+W439K
G305K+W469R
G305K+G476K
G305K+G477R
W439R+W469R
W439R+G476K
W439R+G477R
W469T+G476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+G476K
W140Y+E212D+G305K+G476K
W140Y+G305K+W439R+G476K
W140Y+G305K+W469T+G476K
W140Y+G304R+G476K
W140Y+N260P+G304R+G477K
W140Y+E212D+G304R+G477K
W140Y+G304R+W439R+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+W439R+G477K and
W140Y+G305K+W469T+G477K
wherein the variants has at least 97% and less than 100% sequence identity to the alpha-amylase of SEQ ID NO: 2.

In one embodiment, the variant of invention comprises between 2 and 20 alterations, e.g. between 2 and 10 or between 2 and 5, such as 2, 3, 4, 5, 6, 7, 8, 9 or 10 alterations. Preferably the alterations are substitutions and/or deletions.

In one embodiment, the invention provides variants that consists of 450 to 490, e.g., 460 to 485, 465 to 483, 480 to 483 amino acids, such as 481, 482, 483 or 484 amino acids, preferably 483.

In an embodiment, the variant has sequence identity of at least 60%, e.g., at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent alpha-amylase.

In another embodiment, the variant has at least 60%, e.g., at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 1.

In another embodiment, the variant has at least 60%, e.g., at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, improve wash performance and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In an embodiment, the variant has improved catalytic efficiency compared to the parent enzyme.

In an embodiment, the variant has improved catalytic rate compared to the parent enzyme.

In an embodiment, the variant has improved chemical stability compared to the parent enzyme.

In an embodiment, the variant has improved oxidation stability compared to the parent enzyme.

In an embodiment, the variant has improved pH activity compared to the parent enzyme.

In an embodiment, the variant has improved pH stability compared to the parent enzyme.

In an embodiment, the variant has improved specific activity compared to the parent enzyme.

In an embodiment, the variant has improved stability under storage conditions compared to the parent enzyme.

In an embodiment, the variant has decreased substrate binding compared to the parent enzyme.

In an embodiment, the variant has improved substrate specificity compared to the parent enzyme.

In an embodiment, the variant has improved substrate stability compared to the parent enzyme.

In an embodiment, the variant has improved surface properties compared to the parent enzyme.

In an embodiment, the variant has improved thermal activity compared to the parent enzyme.

In an embodiment, the variant has improved thermostability compared to the parent enzyme.

In another embodiment the variant has improved wash performance, in particular improved wash performance at low temperature compared to the parent enzyme.

Parent Alpha-Amylases

The parent alpha-amylase may be (a) a polypeptide having at least 85% sequence identity to the mature polypeptide of SEQ ID NO: 1; (b) a fragment of the mature polypeptide of SEQ ID NO: 1, which has alpha-amylase activity or (c) a polypeptide having immunological cross reactivity with an antibody raised against the mature polypeptide of SEQ ID NO: 1.

In another aspect, the parent alpha-amylase may be (a) a polypeptide having at least 85% sequence identity to the mature polypeptide of SEQ ID NO: 2; (b) a fragment of the mature polypeptide of SEQ ID NO: 2, which has alpha-amylase activity or (c) a polypeptide having immunological cross reactivity with an antibody raised against the mature polypeptide of SEQ ID NO: 2.

In an aspect, the parent has a sequence identity to the mature polypeptide of SEQ ID NO: 1 of at least 87%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 1.

In an aspect, the parent has a sequence identity to the mature polypeptide of SEQ ID NO: 2 of at least 87%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 2.

In another aspect, the parent comprises or consists of the amino acid sequence of SEQ ID NO: 1. In another aspect, the parent comprises or consists of the amino acid sequence of SEQ ID NO: 2.

In yet another embodiment, the parent is an allelic variant of the mature polypeptide of SEQ ID NO: 1 or 2.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial alpha-amylase. For example, the parent may be a Gram-positive bacterial polypeptide such as a *Bacillus* alpha-amylase. Preferred strains are of *Bacillus* sp. DSM 12650 (the AAI-6 α-amylase) or DSM 12651 (the AAI-10 α-amylase). These strains were deposited on 25 Jan. 1999 under the terms of the Budapest Treaty on the International Recognition of the Deposit of Microorganisms for the Purposes of Patent Procedure at Deutsche Sammmlung von Microorganismen and Zellkulturen GmbH (DSMZ), Mascheroder Weg 1 b, D-38124 Braunschweig DE. Thus, in one aspect the parent is a *Bacillus* AAI-6 alpha-amylase or a *Bacillus* AAI-10 alpha-amylase e.g., the alpha-amylase of SEQ ID NO: 1 or 2. The alpha-amylases of SEQ ID NOs 1 and 2 as well as the variants hereof may also be artificially manufactured by methods known in the art.

Preparation of Variants

The present invention also relates to methods for obtaining a variant having alpha-amylase activity, comprising: (a) introducing into a parent alpha-amylase an alteration at two or more positions corresponding to positions W140; W159; W167, Q169, W189, E194, N260, F262, F289, W284, G304, G305, W347, R439, W469, D476 and G477 of the mature polypeptide of SEQ ID NO: 1, wherein each alteration is independently a substitution, deletion or insertion and the variant has alpha-amylase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-alpha-amylase gene (amyQ), *Bacillus licheniformis* alpha-alpha-amylase gene (amyL), *Bacillus licheniformis* penicillinase gene (penP), *Bacillus stearothermophilus* maltogenic alpha-amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-alpha-amylase, *Aspergillus niger* acid stable alpha-alpha-amylase, *Aspergillus niger* or *Aspergillus awamori* glucoalpha-amylase (glaA), *Aspergillus oryzae* TAKA alpha-amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-alpha-amylase gene in which the untranslated leader has been replaced by an untranslated leader from an *Aspergillus* triose phosphate isomerase gene; non-limiting examples include modified promoters from an *Aspergillus niger* neutral alpha-alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoalpha-amylase, *Aspergillus niger* alpha-glucosidase, *Aspergillus oryzae* TAKA alpha-amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA alpha-amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoalpha-amylase, *Aspergillus niger* alpha-glucosidase, *Aspergillus oryzae* TAKA alpha-amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic alpha-amylase, *Bacillus licheniformis* subtilisin, *Bacillus licheniformis* beta-lactamase, *Bacillus stearothermophilus* alpha-alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral alpha-amylase, *Aspergillus niger* glucoalpha-amylase, *Aspergillus oryzae* TAKA alpha-amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic protein- ase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoalpha-amylase promoter, *Aspergillus oryzae* TAKA alpha-alpha-amylase promoter, and *Aspergillus oryzae* glucoalpha-amylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell, including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising a variant of the present invention. Preferably, the compositions are enriched in such a variant. The term "enriched" means that the alpha-amylase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus Aspergillus, e.g., Aspergillus aculeatus, Aspergillus awamori, Aspergillus foetidus, Aspergillus fumigatus, Aspergillus japonicus, Aspergillus nidulans, Aspergillus niger, or Aspergillus oryzae; Fusarium, e.g., Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides, or Fusarium venenatum; Humicola, e.g., Humicola insolens or Humicola lanuginosa; or Trichoderma, e.g., Trichoderma harzianum, Trichoderma koningii, Trichoderma longibrachiatum, Trichoderma reesei, or Trichoderma viride.

The compositions may be prepared in accordance with methods known in the art and may be in the form of a liquid or a dry composition. For instance, the composition may be in the form of a granulate or a microgranulate. The variant may be stabilized in accordance with methods known in the art.

Detergent Compositions

In one embodiment, the invention is directed to detergent compositions comprising an alpha-amylase variant of the present invention in combination with one or more additional cleaning composition components.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Enzyme of the Present Invention

In one embodiment of the present invention, the a polypeptide of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

A polypeptide of the present invention may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0% to about 40% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0% to about 40% by weight of a zwitterionic surfactant. Non-limiting examples of zwitterionic surfactants include betaine, alkyldimethylbetaine, sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 10% to about 40% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-50% by weight, such as about 10% to about 40%, of a detergent co-builder, or a mixture thereof. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl)ethylidenediamine-N, N, N'-triacetate (HE DTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-20% by weight, such as about 0% to about 10%, of a bleaching system. Any bleaching system known in the art for use in laundry+dish wash+I&I detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

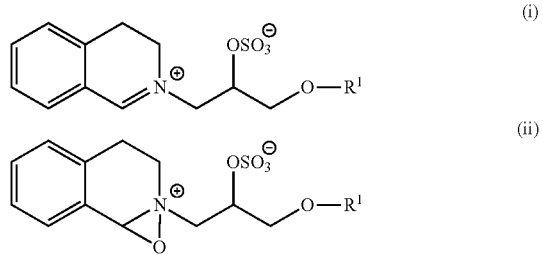

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g. in WO2007/087258, WO2007/087244, WO2007/087259 and WO2007/087242. Suitable photobleaches may for example be sulfonated zinc phthalocyanine.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Additional Enzymes

The detergent additive as well as the detergent composition may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., *Protein Engng*. 4 (1991) 719-737 and Siezen et al. *Protein Science* 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and *subtilisin lentus, subtilisin* Novo, *subtilisin* Carlsberg, *Bacillus licheniformis, subtilisin* BPN', *subtilisin* 309, *subtilisin* 147 and *subtilisin* 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel A G) and KAP (*Bacillus alkalophilus* subtilisin) from Kao.

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Mag-* naporthe grisea (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the 554V variant used in the commercial product Gentle Power Bleach from Huntsman Textile Effects Pte Ltd (WO10/100028).

Amylases:

Suitable amylases which can be used together with the variant of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, (from Novozymes A/S), and Rapidase™, Purastar™/Effectenz™, Powerase and Preferenz S100, Preferenz S110 (from Genencor International Inc./DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent—The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl] benzenesulfonate. Preferred fluorescent whitening agents are Tinopal DMS and Tinopal CBS available from Ciba-Geigy A G, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other Suitable Adjunct Materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms:

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may also be non-aqueous.

Laundry Soap Bars

The alpha-amylases of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an alpha-amylase, optionally one or more additional enzymes, a protease inhibitor, and a salt of a monovalent cation and an organic anion may be prepared and the mixture is then plodded. The alpha-amylase and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

A granular detergent may be formulated as described in WO09/092699, EP1705241, EP1382668, WO07/001262, U.S. Pat. No. 6,472,364, WO04/074419 or WO09/102854.

Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951.

WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905,

WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792,

WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636.

Uses

The present invention is also directed to methods for using the alpha-amylase variants.

The alpha-amylase variants of the invention are useful in detergent compositions, laundry washing, dishwashing and/or cleaning processes at low temperature as well as hard surface cleaning (ADW, car wash, Industrial surface).

Use in Detergents. The polypeptides of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

The detergent composition may further be formulated in unit dosage form or in form a soap bar or a laundry bar, In a specific aspect, the present invention provides a detergent additive comprising a polypeptide of the present invention as described herein. In another aspect, the present invention provides a detergent suited to cleaning at temperatures at or below 35° C.

Methods pNP-G7 Assay for Determination of Alpha-amylase Activity

The alpha-amylase activity may be determined by a method employing the G7-pNP substrate. G7-pNP which is an abbreviation for 4,6-ethylidene($G_7$)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm.). Kits containing G7-pNP substrate and alpha-Glucosidase is manufactured by Roche/Hitachi (cat. No. 11876473).
Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H_4O)_n$ (n=9-10))), 1 mM CaCl2, pH8.0.
Procedure:

The amylase sample to be analyzed was diluted in dilution buffer to ensure the pH in the diluted sample is 7. The assay was performed by transferring 20 μl diluted enzyme samples to 96 well microtiter plate and adding 80 μl substrate working solution. The solution was mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Determination of Binding to Starch
Assay Principle:

Amylase variants are incubated in the presence or absence of insoluble raw rice starch at a selected pH value, in the range of pH 4.0 to 11.0 depending on the intended pH value for the application of the alpha-amylases to be selected; e.g. for detergent applications the pH is suitably selected in the alkaline area such as pH 8.0 or pH10.0; at a selected time, in general between 5 minutes and one hour, preferably in the range of 10 to 30 min such as 10 min or 30 minutes; and at a selected temperature, in general in the range of 0° C. to 30° C., preferably at 4° C. After centrifugation, amylase activity is determined in the supernatants. Difference in activity in the samples incubated in the presence and absence of rice starch is a measure of binding of amylase to insoluble starch.
Materials and Methods:

Rice starch (Sigma Inc, Cat No. S7260), HEPES, Calcium chloride, Triton X-100, Glycine, EnzChek Ultra Amylase Assay Kit (Life Technologies, Cat No. E33651), 96 microwell plates for incubation and dilution (Nunc, Cat No. 269620) and 96 well half-area black plates for fluorescence measurements (Corning, Cat No. 3694).

Assay buffer containing 50 mM HEPES (pH 8.0), 0.1 mM $CaCl_2$ and 0.01% Triton X-100. Enzyme protein solutions are diluted to 0.15 mg/ml with the assay buffer. High pH binding buffer contains 50 mM Glycine-NaOH (pH 10.0) and 0.01% Triton X-100. Rice starch solution (2.5%) is to be prepared in the assay buffer and/or in high pH binding buffer for the variants of SEQ ID NO: 1 and 2. EnzCheck Ultra Amylase substrate solution is prepared according to the manufacturer's instructions and diluted to 50 μg/ml in the assay buffer.

a) Buffer with or without rice starch (2.5%), 100 μl is added to 96 microwell plate and preincubated at 4° C. for 30 min
b) Enzyme solutions, 20 μl are added to the above wells and the plate is placed on a mixer and mixed at 900 rpm for 30 min at 4° C.
c) The plate is centrifuged at 2000 rpm for 5 min at 4° C. for the starch to settle down and the supernatant is carefully removed and diluted to about 1250 times in the assay buffer so that the enzyme protein concentration is about 20 ng/ml.
d) Diluted enzyme samples, 25 μl are added to 96 well half-area black plates containing 25 of EnzCheck Ultra Amylase substrate solution and the plate is immediately placed in a plate reader for fluorescence measurements.
e) Change in fluorescence intensity (Δ F.I.) is measured at 25° C. for 30 min at an excitation wavelength of 485 nm and emission wavelength of 512 nm. Fluorescence readings between the time intervals of 0.5 to 5 min are taken for the calculation of activity (i.e.) change in fluorescence intensity per min (Δ F.I./min).

$$\text{Binding (\%)} = \frac{\text{Activity for without starch} - \text{Activity for with starch}}{\text{Activity for without starch}} \times 100$$

$$\text{Binding relative to parent} = \frac{\text{Binding for variants}}{\text{Binding for parent}}$$

Automatic Mechanical Stress Assay (AMSA) for Laundry

In order to assess the wash performance in laundry, washing experiments are performed using the Automatic Mechanical Stress Assay (AMSA). With the AMSA, the wash performance of many small volume enzyme-detergent solutions can be examined. The AMSA plate has a number of slots for test solutions and a lid that firmly squeezes the textile to be washed against the slot openings. During the wash, the plate, test solutions, textile and lid are vigorously shaken to bring the test solution in contact with the textile and apply mechanical stress in a regular, periodic, oscillating manner. For further description see WO02/42740 especially the paragraph "Special method embodiments" at page 23-24.

The laundry experiments may be conducted under the experimental conditions specified below:

| Detergent dosage | 5 g/L (liquid detergent) |
| --- | --- |
| | 2.5 g/L (powder detergent) |
| Test solution volume | 160 micro L |
| pH | Adjusted to pH 7 or pH 6 (liquid detergent) |
| | As is (powder detergent) |
| Wash time | 20 minutes |
| Temperature | 60° C., 40° C. and 20° C. or 15° C. |
| Water hardness | 15° dH |

Model detergents and test materials may be as follows:

| Laundry liquid model detergent | Sodium alkylethoxy sulfate (C-9-15, 2EO) 6.0% |
| --- | --- |
| | Sodium dodecyl benzene sulfonate 3.0% |
| | Sodium toluene sulfonate 3.0% |
| | Olic acid 2.0% |

| | |
|---|---|
| | Primary alcohol ethoxylate (C12-15, 7EO) 3.0% |
| | Primary alcohol ethoxylate (C12-15, 3EO) 2.5% |
| | Ethanol 0.5% |
| | Monopropylene glycol 2.0% |
| | Tri-sodium citrate dihydrate 4.0% |
| | Triethanolamine 0.4% |
| | De-ionized water ad 100% |
| | pH adjusted to 8.5 with NaOH |
| Laundry powder model detergent | Sodium citrate dihydrate 32.3% |
| | Sodium-LAS 24.2% |
| | Sodium lauryl sulfate 32.2% |
| | Neodol 25-7 (alcohol ethoxylate) 6.4% |
| | Sodium sulfate 4.9% |
| Test material | CS-28 (Rice starch on cotton) |

Test materials are obtained from EMPA Testmaterials AG, Mövenstrasse 12, CH-9015 St. Gallen, Switzerland, from Center For Testmaterials BV, P.O. Box 120, 3133 KT Vlaardingen, the Netherlands, and WFK Testgewebe GmbH, Christenfeld 10, D-41379 Brüggen, Germany.

Water hardness is adjusted to 15° dH by addition of $CaCl_2$, $MgCl_2$, and $NaHCO_3$ ($Ca^{2+}:Mg^{2+}=4:1:7.5$) to the test system. After washing the textiles are flushed in tap water and dried.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore the intensity of the reflected light can be used to measure wash performance.

Colour measurements are made with a professional flat-bed scanner (Kodak iQsmart, Kodak, Midtager 29, DK-2605 Brøndby, Denmark or Expression 10000XL, Epson Danmark, Transformervej 6, 2730 Herlev, Denmark), which is used to capture an image of the washed textile. To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}.$$

Automatic Mechanical Stress Assay (AMSA) for Automatic Dish Wash

Washing experiments are performed in order to assess the wash performance of selected alpha-amylase variants in dishwash detergent compositions. The alpha-amylase variants of the present application may be tested using the Automatic Mechanical Stress Assay (AMSA). With the AMSA, the wash performance of many small volume enzyme-detergent solutions can be examined. The AMSA plate has a number of slots for test solutions and a lid that firmly squeezes the melamine tile to be washed against the slot openings. During the wash, the plate, test solutions, melamine tile and lid are vigorously shaken to bring the test solution in contact with the soiled melamine tile and apply mechanical stress in a regular, periodic oscillating manner. For further description see WO 02/42740 especially the paragraph "Special method embodiments" at page 23-24.

The experiment may be conducted under the experimental conditions as specified in the table(s) below:

| | |
|---|---|
| ADW model detergent with MGDA | MGDA (40%) 30% |
| | Sodium carbonate 20% |
| | Sodium percarbonate 10% |
| | Sodium disilicate 5% |
| | TAED 5% |
| | Sokalan CP5 (39.5%) 10% |
| | Surfac 23-6.5 (100%) 5% |
| | Sodium Sulfate 15% |
| Detergent dosage | 3.33 g/L |
| Test solution volume | 160 micro L |
| pH | As is |
| Wash time | 20 minutes |
| Temperature | 50° C. |
| Water hardness | 17° dH |
| Enzyme concentration in test solution | 0.925, 1.85, 5.55, 11 mg enzyme protein/liter |
| Test material | melamine tiles with starch such as DM-77 and DM-78 |

| | |
|---|---|
| ADW model detergent with STPP | STPP 50% |
| | Sodium carbonate 20% |
| | Sodium percarbonate 10% |
| | Sodium disilicate 5% |
| | TAED 2% |
| | Sokalan CP5 (39.5%) 5% |
| | Surfac 23-6.5 (100%) 2% |
| | Phosphonate 6% |
| Detergent dosage | 3.33 g/L |
| Test solution volume | 160 micro L |
| pH | As is |
| Wash time | 20 minutes |
| Temperature | 50° C. |
| Water hardness | 17° dH |
| Enzyme concentration in test solution | 0.925, 1.85, 5.55, 11 mg enzyme protein/liter |
| Test material | melamine tiles with starch such as DM-77 and DM-78 |

Water hardness is adjusted to 17° dH by addition of $CaCl_2$, $MgCl_2$, and $NaHCO_3$ ($Ca^{2+}:Mg^{2+}=4:1:10$) to the test system. After washing the melamine tiles were flushed in tap water and dried.

The performance of the enzyme variant is measured as the brightness of the colour of the melamine tile washed with that specific alpha-amylase. Brightness can also be expressed as the intensity of the light reflected from the sample when illuminated with white light. When the sample is stained the intensity of the reflected light is lower, than that of a clean sample. Therefore the intensity of the reflected light can be used to measure wash performance of a protease.

Colour measurements are made with a professional flat-bed scanner (Kodak iQsmart, Kodak, Midtager 29, DK-2605 Brøndby, Denmark), which is used to capture an image of the washed melamine tiles.

To extract a value for the light intensity from the scanned images, a special designed software application is used (Novozymes Colour Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int=\sqrt{r^2+g^2+b^2}.$$

Textiles:

Standard melamine tiles with starch such as DM-77 and DM-78 may be obtained from Center For Testmaterials BV, P.O. Box 120, 3133 KT Vlaardingen, the Netherlands.

AMSA Wash Performance

The wash performance of the variants and corresponding parent alpha-amylases is tested by the AMSA-test method as described in the Methods section. The results are given as (performance of variant minus performance of blank) divided by (performance of parent minus performance of blank) multiplied by 100, where the blank is the performance obtained by washing at the same conditions, but in the absence of alpha-amylase.

Terg-O-Tometer (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

TOM Wash Performance

Water hardness is adjusted to the strength described below by addition of $CaCl_2$, $MgCl_2$ and $NAHCO_3$. Wash solutions are prepared with desired amount of detergent, temperature and water hardness in a bucket as described below. Detergent is dissolved during magnet stirring for 10 min.

Temperature and rotation (rpm) in the water bath in the Terg-O-Tometer is set according to the settings below. When temperature is adjusted according to settings (tolerance is +/−0.5° C.) wash solution is added to TOM beaker according to the amount described below.

Agitation in the beaker is at 120 rpm. 2 rice starch swatches (CS-28) and soil ballast are added to each of the beakers and wash carried out according to time stated below. Swatches are rinsed in cold tap water for 5 min. The swatches are left to dry in the dark overnight.

Textile: Textile sample CS-28 (rice starch on cotton) is obtained from Center for Testmaterials BV, P.O. Box 120, 3133 KT Vlaardingen, the Netherlands.

Soil Ballast: Soil ballast Rice starch on cotton/polyester (EMPA 162) is obtained from Center for Testmaterials BV, P.O. Box 120, 3133 KT Vlaardingen, the Netherlands. Bistro gravy (063KC), Frij Chocolate milkshake, Heinz spaghetti (113KC), Herseys double chocolate is obtained from Warwick Equest Ltd, Unit 55, Consett Business Park, Consett, County Durham, DH8 6BN UK

TABLE 1

| Experimental conditions | | |
|---|---|---|
| | European (EU) conditions | Northern America (US) conditions |
| Detergent dosage | 5.77 g/L (liquid detergent) | 0.78 g/L (liquid detergent) |
| Water hardness | 15° dH ($Ca^{2+}$:$Mg^{2+}$:$HCO_3^-$ = 4:1:7.5) | 6° dH ($Ca^{2+}$:$Mg^{2+}$:$HCO_3^-$ = 2:1:4.5) |
| Enzyme concentration in wash solution | 0.25 mg enzyme protein/L | 0.08 mg enzyme protein/L |
| Test solution volume | 500 ml | 800 ml |
| Wash time | 30 minutes | 18 minutes |
| Rotation | 120 rpm | |
| pH | as is | |
| Temperature | 15° C. | |

Detergents and test materials were as follows:

| | |
|---|---|
| Laundry liquid detergent | May be as described below |
| Test material | CS-28 (Rice starch on cotton) |
| Soil ballast | Rice starch on polyester/cotton (EMPA 162), Bistro gravy (063KC), Frij Chocolate milkshake, Heinz spaghetti (113KC), Herseys double chocolate (2 swatches of each) |

The wash performance is measured as the brightness of the color of the textile washed, expressed in remission values. Remission measurements are made using a Macbeth 7000 Color Eye spectrophotometer. Each of the dry swatches is to be measured. As there is a risk of interference from the back-ground, the swatches are placed on top of 4 layers of fabric during the measurement of the remission. The remission is measured at 460 nm. The UV filter is not included. An average result for remission for the swatches is calculated.

Media and Solutions

Cleaning Compositions:

| Model detergents 1 and 2 | | |
|---|---|---|
| Component | Model 1 % w/w | Model 2 % w/w |
| LAS | 12 | 12 |
| AEOS | 4.9 | 4.9 |
| Soap (cocoa) | 2.75 | 2.75 |
| Soap (soya) | 2.75 | 2.75 |
| AEO N25-7 | 11 | 11 |
| NaOH | 1.75 | 1.75 |
| Ethanol | 3 | 3 |
| MPG | 6 | 6 |
| Glycerol | 1.7 | 1.7 |
| TEA | 3.3 | 3.3 |
| Sodium formate | 1 | 1 |
| Sodium citrate | 2 | 2 |
| HEDP | 0 | 0.5 |
| PCA (Sokalan CP-5) | 0.18 | 0.18 |
| Ion exchanged water | 34.2 | 34.2 |
| DTMPA | 0.2 | 0 |

| Model detergent A | | |
|---|---|---|
| Compound | Amount g/100 g | % active ingredient |
| Surfactants | | |
| Na-LAS (92%) (Nacconol 90G) (anionic) | 21.74 | 20 |
| STEOL CS-370E (70%) (anionic) | 14.28 | 10 |
| Bio-soft N25-7 (99.5%) (non-ionic) | 10 | 10 |
| Oleic acid (fatty acid) | 4 | 4 |
| Solvents | | |
| $H_2O$ | 25 | ~33 |
| Ethanol | 0.5 | 0.5 |
| STS (sodium p-toluene sulfonate (40%) | 3.75 | 1.5 |
| Mono propylene glycol | 7 | 7 |
| Builder | | |
| Tri-sodium-citrate | 8 | 8 |
| Triethanolamine (TEA) | 0.5 | 0.5 |
| Inhibitor | | |
| Boric acid | 1.5 | 1.5 |
| Minors | | |
| 10N NaOH (for adjustment to pH 8.5) | 2 | |

| Model detergent X | |
|---|---|
| Compound | wt % |
| Surfactant system | |
| LAS | 15 |
| AEO | 2* |
| soap | 0 |
| Builder system | |
| sodium carbonate | 20 |
| sodium disilicate | 12 |
| zeolite A | 15 |
| PCA | 1 |
| sodium sulfate | 37 |

*Model X is mixed without AEO. AEO is added to the wash separately.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An alpha-amylase variant comprising an alteration at two or more positions corresponding to positions W140, W159, W167, Q169, W189, E194, N260, F262, F289, W284, G304, G305, W347, R439, W469, D476 and G477 of the mature polypeptide of SEQ ID NO: 1, wherein each alteration is independently a substitution, deletion or insertion, and wherein the variant has at least 90%, but less than 100% sequence identity with the mature polypeptide of SEQ ID NO: 1 and wherein the variant has alpha-amylase activity.

2. The variant of claim 1, comprising an alteration at three or more of said positions.

3. The variant of claim 1 comprising an alteration at four or more of said positions.

4. The variant of claim 1 comprising an alteration at five or more of said positions.

5. The variant of claim 1 comprising an alteration at six or more of said positions.

6. The variant of claim 1 comprising an alteration at seven or more of said positions.

7. The variant of claim 1 comprising an alteration at eight or more of said positions.

8. The variant of claim 1 comprising an alteration at nine or more of said positions.

9. The variant of claim 1 wherein the alterations are substitutions.

10. The variant of claim 9, wherein the two or more alterations comprise a substitution of W140ACDEFGHIKLMNPQRSTVY.

11. The variant of claim 9, wherein the two or more alterations comprise a substitution of W159ACDEFGHIKLMNPQRSTVY.

12. The variant of claim 9, wherein the two or more alterations comprise a substitution of W167ACDEFGHIKLMNPQRSTVY.

13. The variant of claim 9, wherein the two or more alterations comprise a substitution of Q169ACDEFGHIKLMNPWRSTVY.

14. The variant of claim 9, wherein the two or more alterations comprise a substitution of W189ACDEFGHIKLMNPQRSTVY.

15. The variant of claim 9, wherein the two or more alterations comprise a substitution of E194ACDWFGHIKLMNPQRSTVY.

16. The variant of claim 9, wherein the two or more alterations comprise a substitution of N260ACFGHIKLMWPQRSTVY.

17. The variant of claim 9, wherein the two or more alterations comprise a substitution of F262ACDEWGHIKLMNPQRSTVY.

18. The variant of claim 9, wherein the two or more alterations comprise a substitution of W284ACDEFGHIKLMNPQRSTVY.

19. The variant of claim 9, wherein the two or more alterations comprise a substitution of F289ACDEWGHIKLMNPQRSTVY.

20. The variant of claim 9, wherein the two or more alterations comprise a substitution of G304ACEFHIKLMNPQRVVTVY.

21. The variant of claim 9, wherein the two or more alterations comprise a substitution of G305ACEFWHIKLMNPQRTVY.

22. The variant of claim 9, wherein the two or more alterations comprise a substitution of W347ACDEFGHIKLMNPQRSTVY.

23. The variant of claim 9, wherein the two or more alterations comprise a substitution of R439ACDEFGHIKLMNPQSTVY.

24. The variant of claim 9, wherein the two or more alterations comprise a substitution of W469ACDEFGHIKLMNPQRSTVY.

25. The variant of claim 9, wherein the two or more alterations comprise a substitution of D476ACEFHIKLMNPQRTVY.

26. The variant of claim 9, wherein the two or more alterations comprise a substitution of G477ACEFHIKLMNPQRTVWY.

27. The variant of claim 9, further comprising a deletion in two positions selected from the group consisting of R181, G182, D183 and G184 when using SEQ ID NO: 1 for numbering, preferably a deletion of R181+D183, or of R181+184, or of R181+G182, or of G182+D183, or of G182+G184, or more preferred of D183 +G184.

28. The variant of claim 9, further comprising at least one of the substitutions selected from the group consisting of: G109A, G149A, K179L, G186A, E190P, N195F, M202LIT, V206YF, N209D, Y243F, S244QAEDN when using SEQ ID NO: 1 for numbering.

29. The variant of claim 9, comprising alterations in positions corresponding to the following positions in SEQ ID NO: 1:
W140Y+Y160S
W140Y+E194D
W140Y+N260P
W140Y+G304K
W140Y+G304R
W140Y+R439T
W140Y+W469T
W140Y+D476K
W140Y+G477R
Y160S+E194D
Y160S+E212D
Y160S+N260P
Y160S+G304K
Y160S+G304R
Y160S+R439T
Y160S+W469T
Y160S+D476K
Y160S+G477R
N260P+G304K
N260P+G305R
N260P+R439K
N260P+W469R N260P+D476K
N260P+G477R
W284G+G304K
W284G+G305R
W284G+R439N
W284G+W469T
W284G+D476K
W284G+G477R
L279T+W284G+H324N+G304K
L279T+W284G+H324N+G305R
L279T+W284G+H324N+R439N
L279T+W284G+H324N+W469T
L279T+W284G+H324N+D476K
L279T+W284G+H324N+G477R
G304K+R439K
G304K+W469R
G304K+D476K
G304K+G477R
G305K+R439K
G305K+W469R
G305K+D476K
G305K+G477R
R439N+W469R
R439N+D476K
R439N+G477R
W469T+D476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+D476K
W140Y+E212D+G305K+D476K
W140Y+G305K+R439N+D476K
W140Y+G305K+W469T+D476K
W140Y+G304R+D476K
W140Y+N260P+G304R+G477K
W140Y+E212D+G304R+G477K
W140Y+G304R+R439N+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+R439N+G477K and
W140Y+G305K+W469T+G477.

30. The variant of claim 9, wherein the alterations consist of the alterations in positions corresponding to the following positions in SEQ ID NO: 1:
W140Y+Y160S
W140Y+E194D
W140Y+N260P
W140Y+G304K
W140Y+G304R
W140Y+R439T
W140Y+W469T
W140Y+D476K
W140Y+G477R
Y160S+E194D
Y160S+E212D
Y160S+N260P
Y160S+G304K
Y160S+G304R
Y160S+R439T
Y160S+W469T
Y160S+D476K
Y160S+G477R
N260P+G304K
N260P+G305R
N260P+R439K
N260P+W469R
N260P+D476K
N260P+G477R
W284G+G304K
W284G+G305R
W284G+R439N
W284G+W469T
W284G+D476K
W284G+G477R
L279T+W284G+H324N +G304K
L279T+W284G+H324N +G305R
L279T+W284G+H324N +R439N
L279T+W284G+H324N +W469T
L279T+W284G+H324N +D476K
L279T+W284G+H324N +G477R
G304K+R439K
G304K+W469R
G304K+D476K
G304K+G477R
G305K+R439K
G305K+W469R
G305K+D476K
G305K+G477R
R439N+W469R
R439N+D476K
R439N+G477R
W469T+D476K
W469T+G477R
W140Y+G304R+G475K
W140Y+N260P+G304R+G475K
W140Y+E212D+G304R+G475K
W140Y+G304R+W438R+G475K
W140Y+G304R+W468T+G475K
W140Y+G305K+G475K
W140Y+N260P+G305K+D476K
W140Y+E212D+G305K+D476K
W140Y+G305K+R439N+D476K
W140Y+G305K+W469T+D476K
W140Y+G304R+D476K
W140Y+N260P+G304R+G477K
W140Y+E212D+G304R+G477K
W140Y+G304R+R439N+G477K
W140Y+G304R+W469T+G477K
W140Y+G305K+G477K
W140Y+W284K+G305K+G477K
W140Y+N260P+G305K+G477K
W140Y+E212D+G305K+G477K
W140Y+G305K+R439N+G477K and
W140Y+G305K+W469T+G477K.

31. The variant of claim 9, which has at least 95%, but less than 100%, sequence identity to the amino acid sequence of SEQ ID NO: 1.

32. The variant of claim 9, which has at least 97%, but less than 100%, sequence identity to the amino acid sequence of SEQ ID NO: 1.

33. The variant of claim 9, which has at least 99%, but less than 100%, sequence identity, to the amino acid sequence of SEQ ID NO: 1.

34. The variant of claim 9, wherein the parent alpha-amylase comprises or consists of the mature polypeptide of SEQ ID NO: 1.

35. A detergent composition comprising a variant alpha-amylase of claim 1.

36. The variant of claim 10, wherein the substitution is W140YFH.

37. The variant of claim 11, wherein the substitution is W159YFH.

38. The variant of claim 12, wherein the substitution is W167YFH.

39. The variant of claim 14, wherein the substitution is W189YFHEDQN.

40. The variant of claim 15, wherein the substitution is E194DNS.

41. The variant of claim 16, wherein the substitution is N260GPA.

42. The variant of claim 17, wherein the substitution is F262P or F262G.

43. The variant of claim 18, wherein the substitution is W284G or W284H.

44. The variant of claim 19, wherein the substitution is F289H.

45. The variant of claim 20, wherein the substitution is G304KRQE.

46. The variant of claim 21, wherein the substitution is G305KRQE.

47. The variant of claim 22, wherein the substitution is W347YFH.

48. The variant of claim 23, wherein the substitution is R439NQT.

49. The variant of claim 24, wherein the substitution is W469T or W469N.

50. The variant of claim 25, wherein the substitution is D476KRQE.

51. The variant of claim 26, wherein the substitution is G477KRQE.

* * * * *

```
                        SEQUENCE LISTING

<160> NUMBER OF SEQ ID NOS: 2

<210> SEQ ID NO 1
<211> LENGTH: 485
<212> TYPE: PRT
<213> ORGANISM: Bacillus sp.

<400> SEQUENCE: 1

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Glu Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ser Asn Arg
                165                 170                 175

Ile Tyr Lys Phe Arg Gly Asp Gly Lys Ala Trp Asp Trp Glu Val Asp
            180                 185                 190
```

```
Thr Glu Asn Gly Asn Tyr Asp Tyr Leu Met Tyr Ala Asp Val Asp Met
            195                 200                 205

Asn His Pro Glu Val Ile Asn Glu Leu Asn Arg Trp Gly Val Trp Tyr
210                 215                 220

Ala Asn Thr Leu Asn Leu Asp Gly Phe Arg Leu Asp Ala Val Lys His
225                 230                 235                 240

Ile Gln Phe Ser Phe Met Arg Asn Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
275                 280                 285

Phe Asp Val Pro Leu His Tyr Asn Leu Tyr Gln Ala Ser Asn Ser Gly
290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
                355                 360                 365

Gly Asp Tyr Tyr Gly Ile Pro Ser Asp Gly Val Pro Ser Tyr Arg Gln
370                 375                 380

Gln Ile Asp Pro Leu Leu Lys Ala Arg Gln Lys Tyr Ala Tyr Gly Pro
385                 390                 395                 400

Gln His Asp Tyr Leu Asp His Pro Asp Val Ile Gly Trp Thr Arg Glu
                405                 410                 415

Gly Asp Ser Ser His Pro Lys Ser Gly Leu Ala Thr Leu Ile Thr Asp
            420                 425                 430

Gly Pro Gly Gly Ser Lys Arg Met Tyr Ala Gly Leu Lys Asn Ala Gly
            435                 440                 445

Glu Thr Trp Tyr Asp Ile Thr Gly Asn Arg Ser Asp Thr Val Lys Ile
450                 455                 460

Gly Ser Asp Gly Trp Gly Glu Phe His Val Asn Asp Gly Ser Val Ser
465                 470                 475                 480

Ile Tyr Val Gln Lys
            485

<210> SEQ ID NO 2
<211> LENGTH: 485
<212> TYPE: PRT
<213> ORGANISM: Bacillus sp.

<400> SEQUENCE: 2

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
```

-continued

```
                65                  70                  75                  80

Thr Lys Ala Glu Leu Glu Arg Ala Ile Arg Ser Leu Lys Ala Asn Gly
                        85                  90                  95

Ile Gln Val Tyr Gly Asp Val Val Met Asn His Lys Gly Gly Ala Asp
                       100                 105                 110

Phe Thr Glu Arg Val Gln Ala Val Glu Val Asn Pro Gln Asn Arg Asn
                       115                 120                 125

Gln Glu Val Ser Gly Thr Tyr Gln Ile Glu Ala Trp Thr Gly Phe Asn
                       130                 135                 140

Phe Pro Gly Arg Gly Asn Gln His Ser Ser Phe Lys Trp Arg Trp Tyr
        145                 150                 155                 160

His Phe Asp Gly Thr Asp Trp Asp Gln Ser Arg Gln Leu Ala Asn Arg
                       165                 170                 175

Ile Tyr Lys Phe Arg Gly Asp Gly Lys Ala Trp Asp Trp Glu Val Asp
                       180                 185                 190

Thr Glu Asn Gly Asn Tyr Asp Tyr Leu Met Tyr Ala Asp Val Asp Met
                       195                 200                 205

Asp His Pro Glu Val Ile Asn Glu Leu Asn Arg Trp Gly Val Trp Tyr
                       210                 215                 220

Ala Asn Thr Leu Asn Leu Asp Gly Phe Arg Leu Asp Ala Val Lys His
        225                 230                 235                 240

Ile Lys Phe Ser Phe Met Arg Asp Trp Leu His Val Arg Gly Gln
                       245                 250                 255

Thr Gly Lys Asn Leu Phe Ala Val Ala Glu Tyr Trp Lys Asn Asp Leu
                       260                 265                 270

Gly Ala Leu Glu Asn Tyr Leu Ser Lys Thr Asn Trp Thr Met Ser Ala
                       275                 280                 285

Phe Asp Val Pro Leu His Tyr Asn Leu Tyr Gln Ala Ser Asn Ser Ser
                       290                 295                 300

Gly Asn Tyr Asp Met Arg Asn Leu Leu Asn Gly Thr Leu Val Gln Arg
        305                 310                 315                 320

His Pro Ser His Ala Val Thr Phe Val Asp Asn His Asp Thr Gln Pro
                       325                 330                 335

Gly Glu Ala Leu Glu Ser Phe Val Gln Gly Trp Phe Lys Pro Leu Ala
                       340                 345                 350

Tyr Ala Thr Ile Leu Thr Arg Glu Gln Gly Tyr Pro Gln Val Phe Tyr
                       355                 360                 365

Gly Asp Tyr Tyr Gly Ile Pro Ser Asp Gly Val Pro Ser Tyr Arg Gln
                       370                 375                 380

Gln Ile Asp Pro Leu Leu Lys Ala Arg Gln Gln Tyr Ala Tyr Gly Arg
        385                 390                 395                 400

Gln His Asp Tyr Phe Asp His Trp Asp Val Ile Gly Trp Thr Arg Glu
                       405                 410                 415

Gly Asn Ala Ser His Pro Asn Ser Gly Leu Ala Thr Ile Met Ser Asp
                       420                 425                 430

Gly Pro Gly Gly Ser Lys Trp Met Tyr Val Gly Arg Gln Lys Ala Gly
                       435                 440                 445

Glu Val Trp His Asp Met Thr Gly Asn Arg Ser Gly Thr Val Thr Ile
                       450                 455                 460
```

```
Asn Gln Asp Gly Trp Gly His Phe Phe Val Asn Gly Gly Ser Val Ser
465                 470                 475                 480
Val Trp Val Lys Arg
                485
```